United States Patent [19]

Dawes et al.

[11] 4,400,547
[45] Aug. 23, 1983

[54] HYDROFORMYLATION PROCESS UTILIZING AN UNMODIFIED RHODIUM CATALYST AND THE STABILIZATION AND REGENERATION THEREOF

[75] Inventors: John L. Dawes, Longview, Tex.; Thomas J. Devon, Kingsport, Tenn.

[73] Assignee: Eastman Kodak Company, Rochester, N.Y.

[21] Appl. No.: 252,753

[22] Filed: Apr. 10, 1981

[51] Int. Cl.$^3$ ............................................. C07C 45/50
[52] U.S. Cl. .................................. 568/454; 568/452; 568/451
[58] Field of Search ................ 568/451, 452, 454, 456

[56] References Cited

U.S. PATENT DOCUMENTS

| | | | |
|---|---|---|---|
| 2,880,241 | 3/1959 | Hughes | 568/451 |
| 3,527,809 | 9/1970 | Pruett et al. | 568/454 |
| 3,871,970 | 3/1975 | Nienburg et al. | 568/454 |
| 3,899,442 | 8/1975 | Friedrich | 568/454 |
| 3,917,661 | 10/1975 | Pruett et al. | 568/454 |
| 4,148,830 | 4/1979 | Pruett et al. | 568/454 |
| 4,135,911 | 1/1979 | Balmat | 568/456 |
| 4,196,096 | 4/1980 | Dawes | 252/414 |

Primary Examiner—Werren B. Lone
Attorney, Agent, or Firm—Donald W. Spurrell; Daniel B. Reece, III

[57] ABSTRACT

This invention concerns an oxo process, either batch or continuously operated, for the preparation of aldehydes, principally in relatively high proportions of branched isomer, from olefins and synthesis gas employing an unmodified rhodium catalyst feed or recycle such as the rhodium salts of organic carboxylic acids. More particularly the invention concerns such a process wherein at least a portion of the reaction medium, e.g., the oxo reactor effluent, is contacted with a ligandizing compound such as triphenylphosphine, prior to product recovery by distillation, such that the rhodium catalyst is converted to a stable form and not lost by plating out on the distillation column or base heater during the distillation. Thereafter, the catalyst is deligandized and regenerated by air treatment and reused in the process.

16 Claims, No Drawings

HYDROFORMYLATION PROCESS UTILIZING AN UNMODIFIED RHODIUM CATALYST AND THE STABILIZATION AND REGENERATION THEREOF

This invention is concerned with a process which may be used in either batch or continuous operation, and in pressure autoclave, liquid-overflow, or other oxo apparatus, for the hydroformylation of olefins in the presence of unmodified rhodium oxo catalyst fed initially or recycled to the reaction zone in a form which can readily form the active catalyst species. More specifically, this invention is concerned with stabilizing the rhodium against plating out during distillation of the reactor effluent by the addition of an organophosphorous or other stabilizing ligand to the effluent prior to distillation.

The present process is principally designed for the preparation of oxo aldehyde products having a relatively high proportion of branched isomer and utilizes an unmodified rhodium oxo catalyst feed in a form such as rhodium carboxylate salts which allows ready complexing in the reaction zone of the rhodium with, e.g., the carbon monoxide and possibly hydrogen of the synthesis (syn) gas to give the active catalyst species. The term "unmodified" as used herein means that the rhodium is not associated with such ligand reactants as the well known phosphines, phosphites, arsines, and stibines disclosed, e.g., in U.S. Pat. No. 3,527,809. The term does allow, however, the various complexes of rhodium with carbon monoxide (hydrogen may also be present in the complex) which form active catalyst species in the reaction zone. Such complexes have been characterized in the art as shown, for example, in U.S. Pat. No. 2,880,241.

One of the important objects of this invention is to optimize production of valuable branched chain aldehyde products relative to yields thereof obtained by unmodified and ligandized, e.g., phosphine modified cobalt oxo catalyst systems which give relatively high ratios of unbranched to branched chain aldehyde products. In the case of butyraldehyde oxo products, the lowest ratio of normal to iso- obtainable with commercial cobalt catalysts is on the order of 1.6 to 1.8. A lower ratio is desirable, however, since isobutylraldehyde is a valuable precursor for such materials as neopentyl glycol, a component of coatings, 2,2,4-trimethyl-1,3-pentanediol monoisobutyrate, a coalescing aid for paints, and for isobutyric acid. Another important branched aldehyde is isovaleraldehyde, a precursor to isovaleric acid which has great value as a nutrient additive for cattle feed. The present process yields high proportions of branched aldehyde products, and in the case of butyraldehyde, the ratio of normal to iso ranges from 0.9 to 1.5.

Although unmodified rhodium catalysts and many of their characteristics in hydroformylation reactions are known and appreciated, one serious problem with their use heretofore has been that in the distillation of the reactor effluent comprised of solvent, catalyst, and product aldehydes, a large portion of the rhodium metal deriving from a break-up of the rhodium-syn gas complex has consistently plated out in the distillation column and/or base heater in a form which is not regenerable in any practical sense. This rhodium loss has rendered such processes uneconomical and as a consequence processes have not heretofore been developed to give the high proportions of branched aldehyde products attained by the present invention.

In the present process, the addition of a stabilizing ligand such as triphenylphosphine to the reactor effluent at a molar ratio of ligand to rhodium of about 1 or greater, preferably 3 or greater, forms a rhodium compound or complex that does not plate out during the effluent distillation. After distillation the ligandized rhodium in the column bottoms is subjected to an air regeneration as disclosed in U.S. Pat. No. 4,196,096, omitting however, the subsequent ligandizing step of that patent. This regeneration restores the oxo activity of the rhodium catalyst and converts it to a soluble form, such as the organic carboxylate, which can rapidly form the active carbonyl complex catalyst species upon reintroduction to the reaction zone. It is important to this invention that the effluent distillation temperature be maintained below about 120° C., preferably below about 110° C., and preferably in the absence of water, to insure that essentially complete catalytic activity is restored by the air regeneration. During the air regeneration, the stabilizing ligand is converted, e.g., to inert phosphine oxides or phosphates which cannot bond to rhodium under hydroformylation conditions, thereby allowing the catalyst solution to be recycled to the reactor without affecting either the branched isomer proportion or the catalytic activity.

The invention is broadly defined therefore, as the process for hydroformylating olefins to produce oxygenated products, principally aldehydes, comprising contacting in a reactor at least one olefin with carbon monoxide and hydrogen in the presence of an unmodified rhodium catalyst for a sufficient period to produce said products, contacting the reactor effluent with a ligand, and distilling the effluent below about 120° C. As an adjunct to the invention, the distillation column base product containing at least about 0.1% by weight of the aldehyde product or added aldehyde is contacted with an oxygen containing gas for a sufficient period to deligandize and regenerate the catalyst which then may be recycled to the oxo reactor. It is noted that if desired for a particular oxo process within the context of the present invention, a portion of the ligandized catalyst after distillation could be recycled to the reactor without air regeneration, although periodic deligandizing and regeneration of the catalyst is necessary to maintain the desired high proportion of branched aldehyde products as well as maintain a high catalytic activity.

In accordance with more specific parameters, the unbranched to branched-chain aldehydes produced are in the ratio of about 1.2 or less, the olefins are either alpha or internal having up to 20 carbon atoms, the hydroformylation temperatures are from about 20° C., to about 300° C., the pressures are from about 15 psig to about 10,000 psig, the ligand reactant is one or more organophosphorous compounds selected from triaryl, alkyl and aralkyl phosphines and phosphites, and the ligandizing reaction temperatures are preferably above about 20° C. under a pressure preferably above about 15 psig. The preferred hydroformylation temperatures are from about 60° C. to about 200° C., and the preferred pressures from about 1,000 to about 5,000 psig. with from about 1,500 to about 3,000 psig being most preferred.

In carrying out the present process in a continuous manner, conventional, continuous oxo equipment well known to those skilled in the art may be used including, for example, oxo reactor, high pressure chiller, vapor-liquid separator, pressure let-down valve, (optional-low boiler removal column for olefins, etc.), product recovery distillation column, (optional-base overflow chiller), air regeneration tank or column, and catalyst recirculation means.

In the operation of a typical continuous process embodying the present invention, the syn gas is introduced into the oxo reactor in a continuous manner by means, for example, of a primary compressor and the ratio of hydrogen to carbon monoxide in the feed may be selected according to the particular olefin being hydroformylated and the reaction conditions present, as is well known in the art. Generally, the molar ratio of hydrogen to carbon monoxide in the reactor will be in the range of 0.5 to 2, but it has been found in many hydroformylations that the rate of reaction as well as yield of the desired product may be increased by increasing the hydrogen to carbon monoxide molar ratio to above 2.0, and ratios up to about 10.0 or more, may be used. The syn gas preferably is present in a molar excess (total moles of $H_2+CO$) with respect to the olefin and the molar ratio varies typically from about 1 to about 10, preferably from above about 1 to about 2.

The olefin is fed to the reactor by means of suitable pumps capable of operating under substantial pressures and the feed rates of the olefin and syn gas are selected to maintain the above recited molar ratios of these reactants in the reactor. Typical useful olefins include $\alpha$-olefins containing from 2 to 20 carbon atoms and preferably from 2 to 10 carbon atoms, straight-chain or branched-chain, and optionally containing groups or substituents which do not interfere with the hydroformylation process. Illustrative such $\alpha$-olefins are ethylene, propylene, 1-butene, 2-methyl-1-butene, 1-pentene, 1-hexene, 1-heptene, 1-octene, 2-ethyl-1-hexene, 1-dodecene and 1-octadecene. Also applicable to the present process are the internal olefins such as butene-2 and cyclic olefins such as cyclooctene.

If desired, mixtures of olefins can be fed to the reaction zone simultaneously. For example, the present process can be used to hydroformylate a mixture of propylene, isobutylene and butene-1 at production rates essentially equivalent to that achieved with propylene alone. This unique aspect provides a definite advantage over prior art processes in producing a mixture of different carboxaldehyde products, especially if the olefin feed contains branched or otherwise hindered olefins which are typically slow to hydroformylate by prior processes. Moreover, the multiple hydroformylations can be carried out in one reactor zone, whereas prior processes normally require separate reaction zones and different reaction conditions for each of the olefins in the feed mixture. Also, the intrinsic unbranched to branched-chain product ratio obtained from the present process is not significantly altered by the presence of such mixed olefin feeds, and it has been observed that in the case of the aforesaid feed mixture of propylene, butene-1, and isobutylene, the normal to isobutyraldehyde product ratio is the same as that from propylene feed alone.

The rhodium is introduced into the reactor zone along with the solvent through suitable liquid pressure pumping means and interacts with the syn gas to form a complex, active catalyst species. The rhodium may be introduced in virtually any form such as organic or mineral acid salts which will permit it to complex with the syn gas. The organic salts are typically acetates, butyrates, octanoates and the like while the mineral acid salts include chlorides, sulfates, sulfonates and the like. Preferred are the carboxylates which are readily prepared by the reaction of aqueous solutions of alkali metal carboxylates with rhodium trichloride. The recycled, air-regenerated rhodium is introduced into the reactor also as a soluble material such as the carboxylate salt of the acid formed from the oxo aldehyde product present during the air regeneration step.

Any suitable solvent which does not adversely effect the process and which is inert with respect to the catalyst, olefin feed, synthesis gas and the hydroformylation products may be used. Inert solvents of this nature are well known to those skilled in the art and include xylene and their substituted derivatives, pentanes, naphtha, kerosene, mineral oils, cyclohexane, cyclopentane, ethers, esters, etheresters, alcohols, acetals, ketones and preferably benzene, toluene, ethanol, isopropanol, ethylene glycol monomethylether and ethylene glycol dimethylether, and most preferably 2,2,4-trimethyl-1,3-pentanediol monoisobutyrate (TMPDMI), and its isomers, and the by-products such as alcohols, esters, acetals, and hydroxyaldehydes produced in the hydroformylation reaction and retained as high boiling liquids at the bottom of the distillation column. The solvent system, preferably a high boiler, is introduced into the reactor along with the catalyst and allowed to recycle therewith after the distillation and catalyst regeneration steps.

The present process can be carried out with very small amounts of catalyst such as that containing about $1 \times 10^{-6}$ moles of rhodium (metal) per mole of olefin feed. However, such low catalyst concentrations are not commercially desirable since the reaction rates are low. The upper catalyst concentration is essentially unlimited and appears to be dictated principally by the high cost of rhodium and the fact that no advantage is evident in the use of catalyst containing above about $1 \times 10^{-1}$ moles of rhodium per mole of olefin. A concentration of rhodium (metal) of from about $1 \times 10^{-5}$ moles to about $5 \times 10^{-2}$ moles per mole of olefin is preferred, and from about $1 \times 10^{-4}$ to about $1 \times 10^{-2}$ is most preferred.

The continuous oxo apparatus may be operated in a number of ways to give the desired low ratio of unbranched to branched hydroformylation products. It is preferred, however, that the reactor be operated as a liquid-overflow reactor using a side take-off for product effluent containing catalyst, solvent, and gases which are passed through a chiller if desired to reduce the amount of product in the vapor phase. The stabilizing ligand is introduced into the pressurized effluent which is then fed to a vapor/liquid separator unit wherein the syn gas, olefin and other volatile gases are phase separated from the effluent leaving only the liquid residue comprising liquid hydroformylation products, solvent and now ligand stabilized catalyst. The separated gases may be recycled immediately to the reaction zone. The liquid residue is removed from the vapor/liquid separator and passed through a pressure let-down valve to the distillation zone or unit.

Any of a large variety of ligands may be used to stabilize the rhodium and which can be transformed subsequently to inactive oxides or other inactive compounds in the air regeneration step. Suitable ones include trialkylphosphites, tricycloalkylphosphites, triarylphosphites, triarylphosphines, triarylstibines, and triarylarsines. Preferably, each organo moiety in the ligand should not exceed 18 carbon atoms. Typical are trimethylphosphite, triethylphosphite, butyldiethylphosphite, tri-n-propylphosphite, tri-n-butylphosphite, tri-2-ethylhexylphosphite, tri-n-octylphosphite, tri-n-dodecylphosphite, triphenylphosphite, trinaphthylphosphite, triphenylphosphine, tri(p-chlorophenyl)-phosphite, trinaphthylphosphine, phenyldiphenylphosphine, diphenylphenylphosphonite, diphenylethylphosphonite, triphenylarsine, triphenylstibine, tris(p-chlorophenyl)phosphine, tri(p-cyanophenyl)phosphite, tri(p-methoxyphenyl)phosphite, ethyldiphenylphosphinite, and the like. Triphenylphosphite and triphenylphosphine are the most preferred.

The ligandizing step may be carried out at temperatures between about 20° C. and 160° C. and at pressures between about 15 psig and 3000 psig. The lower temperatures require lower pressures. It is preferred, however, in order to allow complete rhodium stabilization, that the ligand be added to the reactor effluent after it has left the reaction zone and before its pressure is permitted to drop below about 2000 psig and its temperature below about 100° C. If the ligandizing occurs in the reactor zone it alters the ratio of unbranched to branched-chained aldehyde products being formed therein and changes the catalyst character. Ligand addition is conveniently done in the continuous apparatus described above by pumping ligand into the reactor effluent before it reaches the aforesaid pressure letdown valve. As will be appreciated, however, any number of points between the reaction zone and the distillation zone will have suitable pressure and temperature conditions for carrying out the ligandizing reaction.

The air regeneration step may be carried out at atmospheric conditions in simple equipment and is disclosed in detail in U.S. Pat. No. 4,196,096. Preferably, the operation is carried out in a tank with continuous feed and continuous removal of regenerated catalyst. This regeneration requires the presence of at least a minute amount of aldehyde and works satisfactorily with as little as 0.1 percent aldehyde by weight of base product in the regeneration apparatus. The aldehyde can be provided by adjusting the distillation zone operating conditions to leave sufficient aldehyde in the base product, or the aldehyde may be added to the regeneration apparatus. It is preferred that the aldehyde be present in a molar ratio to the rhodium of from about 2 to about 5. Theoretically, a mole or rhodium and a mole of ligand would require the presence of about 2.05 moles of aldehyde. The aldehyde preferably is one produced by the hydroformylation reaction, such as iso or normal butyraldehyde, propionaldehyde, or a low boiling aldehyde such as acetaldehyde. The air or oxygen is blown through the stabilized catalyst solution at a low rate to prevent a rapid temperature rise, and as regeneration proceeds the solution goes from black to a straw color which allows its progress to be monitored visually. The regeneration can take up to 48 hours or more and excess aldehyde and any acids formed are then optionally removed. The amount of aldehyde and air used in the regeneration are controlled to minimize the formation of acid. The regenerated catalyst solution may then be treated by suitable means such as filtration, if necessary, to remove any solids such as triphenylphosphine oxide, and returned to the reaction zone.

The following examples further illustrate the present invention and should not be construed as limiting the invention in any manner.

EXAMPLE 1

Preparation of Rhodium Isobutyrate

An aqueous solution of sodium isobutyrate is prepared by dissolving 4 grams of sodium hydroxide and 9 grams of isobutyric acid in 100 milliliters of water at room temperature. Hydrated rhodium trichloride (2.5 grams) is added to the aqueous solution and stirred at room temperature until complete solution occurs. The bright red solution is heated with stirring on a rotary evaporator at 100° C. for 1 hour, during which time a yellow green precipitate of rhodium isobutyrate forms. The mixture is cooled and the precipitate removed by filtration on a fine glass frit. The precipitate is washed thoroughly with water and dried under a stream of dry nitrogen. The precipitate is then dissolved in about 60 milliliters of pure isobutyric acid and filtered through a fine glass frit to remove traces of insoluble material. A suitable volume of this solution is made up with more isobutyric acid to give a known rhodium metal concentration.

EXAMPLE 2

Oxo effluent (approximately 182 liters) was prepared in a typical continuous process and apparatus for use in a series of laboratory scale distillation experiments described below. The preparation was as follows:

Sufficient rhodium isobutyrate solution from Example 1 was added to 120 liters of TMPDMI solvent to give a rhodium (metal) concentration of 2 $\mu$g/ml of solution. This solution was fed to a stainless steel pressure reactor of 0.6 cu. ft. volume provided with an effluent side draw. The catalyst was contacted within the reactor with propylene and syn gas (48% Co, 52% $H_2$) at 150° C. The hydroformylation proceeded with a catalyst residence time of 30 minutes and the reactor effluent was passed through a cooling heat exchanger under pressure, then through a high pressure vapor/liquid separator, and the liquid then passed through a pressure letdown valve into a tank where unreacted propylene was removed at room temperature. The mixture of catalyst solution and butyraldehyde product was pumped out of this let-down tank into polypropylene jugs which were stored under nitrogen at 5° C.

EXAMPLE 3

This example gives the general distillation procedure for the reactor effluent from Example 2 as follows:

Reactor effluent (2 liters) prepared in Example 2 is carefully transferred in the absence of air from one of the jugs into a two-liter graduated transfer vessel and then into a stainless steel distillation column to a level of 200 ml. The distillation is initiated by starting the base heater set at 110° C., reboiler circulation pump, water feed into the column base at 100 ml/hour, and the base take off pump set at 600 ml/hr in concert with a column feed pump which pumps reactor effluent into the column at a rate to hold the column level at 200 ml. Water and butyraldehyde are distilled overhead and catalyst base product pumped into a lower 250 ml base product tank to bring the column to equilibrium, after which the base product (steady state) is collected in an upper 250 ml base product tank for 30 minutes. Approximately 200 ml of the steady state base product, hereinafter referred to as SSBP, is collected and the column shut down. The column feed (CF) was analyzed by gas-liquid chromatography and contains 77% TMPDMI by weight and 1.54 μg of rhodium/ml of CF. Gas liquid chromatographic and atomic absorption spectroscopic techniques have shown that no rhodium or TMPDMI is distilled overhead.

EXAMPLE 4

This example gives the general procedure used for the examples herein to evaluate the catalytic activity of the various air regenerated CF and SSBP. According to the procedure the CF or SSBP is weighed and charged into a 300 ml autoclave (Hastelloy C Autoclave Engineers Magnedrive). The autoclave is sealed, purged with nitrogen, chilled with dry ice and acetone and charged with propylene (45 g.). The autoclave is then pressured to 2000 psig with syn gas (48% CO, 52% $H_2$), heated to 150° C., and the pressure brought to 2500 psig with syn gas. The reaction proceeds at these conditions for 30 minutes and as the pressure drops to about 2300 psig during this period it is brought back to 2500 psig with syn gas. The autoclave is then cooled to room temperature and vented to remove syn gas and unreacted propylene. The weight gains of the CF and SSBP catalyzed hydroformylations are then compared.

EXAMPLE 5

In this example the SSBP of Example 3 was analyzed chromatographically and contained 91% TMPDMI by weight. A 65 ml sample of column feed and a 55 ml sample of said SSBP were taken according to the relationship; mls of SSBP=(% TMPDMI in CF/% TMPDMI in SSBP)×mls of CF. It is noted that if no rhodium were lost during distillation, the SSBP would also have a rhodium concentration of 1.54 μg/ml. Both samples were regenerated by purging with air at room temperature for 15 minutes and evaluated for oxo activity (a measure of the amount of rhodium lost during distillation) using the procedure described in Example 4. The CF produced 35.68 g of butyraldehyde while the SSBP produced only 13.33 g which represents for the SSBP a very low catalytic activity of the CF and indicates a large rhodium loss.

EXAMPLE 6

This example demonstrates the stabilizing effect on the rhodium during distillation in the presence of water, of triphenyl phosphine in various molar ratios, as given in Table 1 below. The runs were made as follows:

Two liters of reactor effluent from Example 2 is pressurized, in the absence of air, into a two-liter transfer flask. The concentration of Rh is 1.54 μg/ml for a total charge of 3.08 mg of Rh in the two liters of solvent. Triphenylphosphine (23.5 mg for a 3/1 molar ratio of $\phi_3$P/Rh and 11.75 mg. for a 1.5/1 ratio), dissolved in a solvent, is injected into the transfer vessel and mixed well with the reactor effluent. This system is then distilled as in Example 3. Each CF and SSBP was air regenerated and tested for oxo activity using the procedure of Example 4. The butyraldehyde production of each CF and SSBP set were compared.

TABLE 1

| $\phi_3$P/Rh Mole Ratio | Activity of SSBP Compared to CF |
|---|---|
| 0 | 37.7% (from Example 5) |
| 1.5 | 62.7% |
| 3.0 | 82.8% |

EXAMPLE 7

This example shows that the absence of water, i.e., dry distillation, is preferable. Two dry distillations were carried out, one without added triphenylphosphine and the other with, and compared to the wet distillations of Examples 5 and 6 (approximately), as follows:

A first dry distillation of the reactor effluent of Example 2 was carried out using the distillation procedure described in Example 3. No triphenylphosphine was added to the 2-liter transfer vessel and no water was fed to the column base. The base temperature was set at 110° C. and all the pumping rates were set as in Example 3. The SSBP and CF were air regenerated and tested for oxo activity using the procedure of Example 4. The SSBP had 41.1% the activity of the column feed.

A second dry distillation was carried out as above with triphenylphosphine mixed into the reactor effluent of Example 2 in a $\phi_3$P/Rh molar ratio of 2.55. The column base temperature was set at 110° C. and all the pumping rates were set as in Example 3, except that no water was pumped into the base. The SSBP had 96.4% the activity of the CF. Table 2 below summarizes these results with the molar ratios of ligand to rhodium in parenthesis.

TABLE 2

| | % Recovered Oxo Activity | |
|---|---|---|
| Stabilizer | Dry Distillation | Wet Distillation |
| None | 41% | 37% (Example 5) |
| $\phi_3$P | 96% (2.55, $\phi_3$P/Rh) | 82% (3.0, $\phi_3$P/Rh) (Example 6) |

Examples 8-12 show the relationship of distillation base temperature to the stability of 3/1 molar $\phi_3$P/Rh catalyst, as measured by the relative activity in the hydroformylation of butene-1 to valeraldehyde. For these examples, reactor effluent from a pilot plant overflow reactor was contacted with the $\phi_3$P, let down in pressure and separated from unreacted butene. The liquid effluent containing 34% valeraldehyde and 66% high boilers was then collected under nitrogen in a 6 gal polypropylene jug and used in all the distillation experiments of Examples 8-12. The distillation apparatus is designed to operate under vacuum, the column packing is stainless steel Penn State Packing and the base pot contains stainless steel turnings. The column was operated without water addition at base temperatures of 100°, 119°, 139°, 158° and 166° C., with a catalyst residence time in the column base for each distillation of 20 minutes. The pressure in the column was adjusted such that the concentration of high boiling solvent (heavy by-products) in the column base remained constant at 90–92%. Thus, the column was operated at 100° C. at 100 mm Hg, 119° C., at 233 mm Hg, 139° C. at 413 mm Hg, and the runs at 158° C. and 166° C. were run at 760 mm Hg. The steady state column base product (SSBP) and column feed (CF) were air regenerated separately but in exactly the same manner and each tested for oxo activity in the hydroformylation of butene-1 as shown below.

The specific distillation procedure is as follows:

The polypropylene jug is connected to the distillation apparatus and two-liters of the effluent drained by siphon into a two-liter graduated feed tank. The base pot (500 ml volume) contains 304 stainless steel turnings. Vacuum (100 mm Hg) is applied to the column and the effluent fed to the column to the 250 ml level mark on the base pot. The base temperature desired is set using a I²R controller. A reflux splitter on the top of the column is set at 50% take-off and the column feed rate maintains the pot level at the 250 ml. mark. The column base temperature is equilibrated at the desired temperature and the base overflow vacuum pump then started up (set at 20 mm Hg) and the base overflow needle valve adjusted to remove liquid from the column base at 12.5 ml/minute. The needle valve feeding the column is adjusted to hold the base level at 250 ml. Valeraldehyde product, free from high boiling by-products and rhodium is collected pure as overhead product. The column is brought to steady state operating conditions for 20 minutes and the base overflow forerun collected in the bottom 500 ml receiving flask. After attaining steady state conditions, SSBP is collected in the upper 500 ml receiving flask until 200 mls is collected. The column is then shut down and the vacuum replaced with nitrogen.

The hydroformylation activity of air regenerated SSBP was then compared against the hydroformylation activity of air regenerated CF. The CF and SSBP catalyst charge is for each, that amount containing a total of 75 ml of high boiling solvent. Thus, for the CF of these examples, which contains 34% valeraldehyde and 66% high boiling solvent, a charge of 114 ml was used. Similarly, and exemplary, a charge of 82 ml of SSBP from the 100° C. base temperature distillation was used which contained 8.4% valeraldehyde and 91.6% high boiling solvent determined by gas/liquid phase chromatographic analysis.

The air regeneration procedure for both the CF and SSBP catalyst charges comprises placing the charge in a 250 ml graduated cylinder warmed to 50° C., and bubbling air therethrough via a glass frit (setting of 6 on a 15 range, ⅛" saphire rotometer) for 30 minutes. Each charge is then cooled to room temperature and added to a 300 ml Hastelloy C Autoclave Engineers Magnedrive autoclave with cooling control and the net weight charged recorded. The autoclave is sealed, purged with nitrogen, charged with 45 g of butene-1, and then pressured to 2000 psig with synthesis gas (1/1, H₂/CO mole ratio) and heated to 155° C. The pressure is adjusted to 2500 psig and the reaction carried out at 155° at 2500 psig for 15 minutes. The run is cooled to 60° C. and the autoclave vented slowly to remove unreacted gases. The autoclave is cooled further to room temperature and the product weighed. The air regenerated SSBP from the distillation run carried out at a base temperature of 100° C. made 57.9 g of valeraldehyde product compared to 58.5 g of valeraldehyde product made by the air regenerated CF. The regenerated catalyst thus had 99% of its original activity after passing through the column. The other SSBP taken at 119° C., 139° C., 158° C. and 166° C. were evaluated similarly. Table 3 summarizes the results.

TABLE 3

| Ex. No. | Base Temp. °C. | CF Valeraldehyde Yield, g. | SSBP Valeraldehyde Yield, g. | % Activity Retained After Distillation |
|---|---|---|---|---|
| 8 | 100 | 58.50 | 57.90 | 99 |
| 9 | 119 | 60.37 | 57.38 | 95 |
| 10 | 139 | 62.65 | 52.00 | 83 |
| 11 | 158 | 60.37 | 41.38 | 69 |
| 12 | 166 | 56.39 | 31.58 | 56 |

The above data shows that column base temperatures above about 120° C. are detrimental to the regeneration of oxo activity due to the physical loss of rhodium through plating, since no rhodium is observed in the overhead product. Table 4 below records rhodium concentrations in the four base products 8–11, from the above examples. The samples were analysed using atomic absorption analysis and show the trend that rhodium is physically removed from the catalyst at higher base temperatures.

TABLE 4

| Base Product | Base Temp. °C. | Rhodium Concentration in Base Product ppm |
|---|---|---|
| 8 | 100 | 6.4 |
| 9 | 119 | 4.6 |
| 10 | 139 | 4.2 |
| 11 | 158 | 3.2 |

EXAMPLE 13—SIMULTANEOUS HYDROFORMYLATIONS

A catalyst solution was prepared by adding a sufficient amount of a solution of rhodium isobutyrate in isobutyric acid to 600 ml of TMPDMI to give a rhodium concentration of $9.71 \times 10^{-5}$ moles of Rh in the total catalyst solution, and charged into a nitrogen purged 2-liter autoclave. Isobutylene (47 grams) was transferred into a bomb chilled in dry ice, the bomb attached to the autoclave and the liquified olefin pressured out into the autoclave by 100 psig syn gas (H₂/CO molar ratio=1/1). The autoclave was blocked in and the bomb removed. Butene-1 (120 grams) was charged in a similar manner by pressuring to 500 psig. Propylene (150 grams) was charged in the same manner by pressuring to 1,500 psig. Thus, the rhodium concentration in the reactor is $1.48 \times 10^{-5}$ moles of Rh per mole of olefin feed. The autoclave was then heated to 150° C. over 25 minutes and maintained at this temperature during the hydroformylation, and the total pressure was brought to 2,500 psig and maintained between 2,300 psig and 2,500 psig by repressuring with synthesis gas. The run was carried out for two hours in this manner at which point no more gas uptake was observed. The autoclave was cooled to 60° C., vented, cooled to room temperature and the product drained. This run made 504 grams of carboxaldehyde product. A second run carried out in the same manner made 463 grams of product. The two runs were combined and analyzed by gas chromatography. The normal butyraldehyde/isobutyraldehyde mole ratio was 0.975, the same ratio that is obtained by the hydroformylation of propylene alone using rhodium isobutyrate catalyst feed.

The invention has been described in detail with particular reference to preferred embodiments thereof, but it will be understood that variations and modifications can be effected within the spirit and scope of the invention.

We claim:

1. A hydroformylation process comprising contacting at least one olefin of from 2 to 20 carbon atoms in a reaction zone at a temperature of from about 20° C. to about 300° C. and a pressure of from about 15 psig to about 10,000 psig with hydrogen, carbon monoxide and a catalyst consisting essentially of unmodified rhodium for a sufficient period of time to produce aldehyde product, contacting reactor effluent with at least one ligand selected from trimethylphosphite, triethylphosphite, butyldiethylphosphite, tri-n-propylphosphite, tri-n-butylphosphite, tri-2-ethylhexylphosphite, tri-n-octylphosphite, tri-n-dodecylphosphite, triphenylphosphite, trinaphthylphosphite, triphenylphosphine, tri(p-chlorophenyl)phosphite, trinaphthylphosphine, phenyldiphenylphosphinite, diphenylphenylphosphonite, diphenylethylphosphonite, triphenylarsine, triphenylstibine, tris(p-chlorophenyl)phosphine, tri(p-cyanophenyl)phosphite, tri(p-methoxyphenyl)phosphite, and ethyldiphenylphosphinite, and separating said product from said effluent in a distillation zone at a temperature of about 120° C. or less to leave a base product.

2. The hydroformylation process according to claim 1 wherein the base product is treated with an oxygen containing gas at a suitable temperature for a sufficient period of time to deligandize and regenerate said catalyst to an active hydroformylation catalytic state.

3. The hydroformylation process according to claim 2 wherein said regenerated catalyst is returned to said reaction zone.

4. The hydroformylation process according to claim 1 wherein said reaction zone is operated at a temperature of between about 60° C. and 200° C.

5. The hydroformylation process according to claim 1 wherein said reaction zone is operated at a pressure of between about 1500 psig and 3,000 psig.

6. The hydroformylation process according to claim 1 wherein the molar ratio of said hydrogen to carbon monoxide is at least 0.5.

7. The hydroformylation process according to claim 6 wherein the total moles of hydrogen and carbon monoxide are present in said reaction zone in the ratio range of from 1 to about 10 with respect to moles of said olefin.

8. The hydroformylation process according to claim 1, wherein said alpha olefin is selected from one or more of ethylene, propylene, 1-butene, 2-methyl-1-butene, 1-pentene, 1-hexene, 1-heptene and 1-octene.

9. The hydroformylation process according to claim 1 wherein a solvent is employed from the group consisting of benzene, toluene, ethanol, isopropanol, ethylene glycol monomethylether, ethylene glycol dimethylether, and 2,2,4-trimethyl-1,3-pentanediol monoisobutyrate, and the by-product high-boiler mixture collected as the bottoms of said distillation zone.

10. The hydroformylation process according to claim 1 wherein said unmodified rhodium catalyst is supplied to said reactor zone in the form of a rhodium carboxylate or salt of a mineral acid.

11. The hydroformylation process according to claim 8 wherein said unmodified rhodium catalyst is present in said reaction zone in an amount of between about $1 \times 10^{-6}$ to about $1 \times 10^{-1}$ mol. of rhodium metal per mol of said alpha olefin.

12. The hydroformylation process according to claim 1 wherein said ligand is selected from triphenylphosphine and triphenylphosphite.

13. The hydroformylation process according to claim 1 wherein the molar ratio of ligand to said rhodium metal is at least 1.

14. The hydroformylation process according to claim 1 wherein said distillation zone is operated at a temperature of less than 120° C.

15. The hydroformylation process according to claim 2 wherein at least 0.1 percent of an aldehyde by weight of said base product is blended with said base product prior to treatment thereof with said oxygen containing gas.

16. The hydroformylation process according to claim 15 wherein said oxygen containing gas is air.

* * * * *